(12) United States Patent
Kamberov et al.

(10) Patent No.: US 10,301,660 B2
(45) Date of Patent: May 28, 2019

(54) METHODS AND COMPOSITIONS FOR REPAIR OF DNA ENDS BY MULTIPLE ENZYMATIC ACTIVITIES

(71) Applicant: Takara Bio USA, Inc., Mountain View, CA (US)

(72) Inventors: Emmanuel Kamberov, Ann Arbor, MI (US); John Langmore, Ann Arbor, MI (US); Tim Tesmer, Pinckney, MI (US); Marta Gonzalez-Plasky, Ann Arbor, MI (US)

(73) Assignee: TAKARA BIO USA, INC., Mountain View, CA (US)

( * ) Notice: Subject to any disclaimer, the term of this patent is extended or adjusted under 35 U.S.C. 154(b) by 370 days.

(21) Appl. No.: 15/085,456

(22) Filed: Mar. 30, 2016

(65) Prior Publication Data

US 2016/0289723 A1   Oct. 6, 2016

Related U.S. Application Data

(60) Provisional application No. 62/139,951, filed on Mar. 30, 2015.

(51) Int. Cl.
*C12P 19/34* (2006.01)
*C12N 9/12* (2006.01)
*C12N 9/22* (2006.01)
*C12N 15/10* (2006.01)

(52) U.S. Cl.
CPC ............ *C12P 19/34* (2013.01); *C12N 9/1205* (2013.01); *C12N 9/1252* (2013.01); *C12N 9/22* (2013.01); *C12N 15/1093* (2013.01); *C12Y 207/01078* (2013.01); *C12Y 207/07007* (2013.01); *C12Y 301/11002* (2013.01)

(58) Field of Classification Search
CPC ............ C12N 15/1093; C12N 9/1205; C12N 9/1252; C12N 9/22; C12P 19/34; C12Y 207/01078; C12Y 207/07007; C12Y 301/11002
USPC ........................................................ 435/6.1
See application file for complete search history.

(56) References Cited

U.S. PATENT DOCUMENTS

| | | | |
|---|---|---|---|
| 6,828,098 B2 | 12/2004 | Langmore et al. | |
| 7,270,958 B2 | 9/2007 | Makarov et al. | |
| 2004/0185484 A1 | 9/2004 | Costa et al. | |
| 2013/0244885 A1 | 9/2013 | Wang et al. | |
| 2017/0088887 A1* | 3/2017 | Makarov ............. | C12Q 1/6806 |

FOREIGN PATENT DOCUMENTS

| | | |
|---|---|---|
| CN | 103667442 | 3/2014 |
| EP | 2725125 | 4/2014 |
| EP | 2792751 | 10/2014 |
| WO | WO 1998/039485 | 3/1998 |
| WO | WO 2004/081183 | 9/2004 |
| WO | WO 2014/014497 | 1/2013 |
| WO | WO 2013/163152 | 4/2013 |
| WO | WO 2014/047561 | 3/2014 |
| WO | WO 2014/071295 | 5/2014 |

OTHER PUBLICATIONS

"PureGenome™ High Efficiency Next Generation Sequencing (NGS) Library Preparation Reagents," No. TB574, Ref. A 0812, Jan. 1, 2012.
Klett et al., "Exonuclease VI, a new nuclease activity associated with E. coli and DNA polymerase," *Proc. Natl. Acad. Sci. USA*, 60(3):943-650, 1968.
PCT International Search Report and Written Opinion issued in International Application No. PCT/US2016/024976, dated Jun. 3, 2016.
Son et al., "Preparing DNA libraries for multiplexed paired-end deep sequencing for illumine GA sequencers," In: Current Protocols in Microbiology, John Wiley & Sons, Inc., Hoboken, NJ, USA, 14 pages, Feb. 1, 2011.
White et al., "Genetic mapping of xthA, the structural gene for exonuclease III in *Escherichia coli* K-12," *Journal of Bacteriology*, 126(3):1082-1088, 1976.

* cited by examiner

*Primary Examiner* — Cynthia B Wilder
(74) *Attorney, Agent, or Firm* — Jenny Buchbinder; Bret E. Field; Bozicevic, Field & Francis LLP (57) ABSTRACT

Provided herein are compositions for and methods of generating ligation-competent nucleic acids. In some aspects, the compositions comprise Exonuclease III, T4 DNA Polymerase, Klenow, and/or T4 polynucleotide kinase.

36 Claims, 10 Drawing Sheets

METHODS AND COMPOSITIONS FOR REPAIR OF DNA ENDS BY MULTIPLE ENZYMATIC ACTIVITIES

The present application claims the priority benefit of U.S. provisional application No. 62/139,951, filed Mar. 30, 2015, the entire contents of which is incorporated herein by reference.

BACKGROUND OF THE INVENTION

1. Field of the Invention

The present invention relates generally to the field of molecular biology. More particularly, it concerns compositions for and methods of nucleic acid repair.

2. Description of Related Art

There are several commercial formulations that use T4 DNA Polymerase (T4Pol) and T4 Polynucleotide Kinase (T4PNK) to repair DNA ends prior to ligation for the purposes of cloning or Next Generation Sequencing (NGS). Some formulations also include the Large Klenow fragment of *E. coli* DNA Polymerase I (Klenow) to facilitate complete extension of 3' recessed ends and to prevent over-trimming by the 3' exonuclease activity of T4Pol. Very little attention has been paid to a different form of damage that involves the presence of a phosphate group at the 3' terminus of DNA. Ends containing a 3' phosphate are not extendable and not competent for ligation. The removal of the 3' phosphate is critical for successful and efficient end-repair. Generally, the removal of the 3' phosphate is left to the rather weak 3' phosphatase activity of T4PNK.

SUMMARY OF THE INVENTION

Provided herein is a composition for nucleic acid end-repair that involves multiple enzymatic activities with greatly improved performance over current commercial formulations. The present composition improves the utilization of damaged DNA from clinical samples in NGS library preparations and increases the sensitivity of NGS library preparation.

In one embodiment, there are provided compositions comprising T4 DNA polymerase, T4 polynucleotide kinase, exonuclease III, and Klenow in a suitable buffer. In some aspects, a suitable buffer may comprise substituents that are cofactors, or which affect pH, ionic strength, etc. In some aspects, the composition further comprises a nucleic acid molecule. In some aspects, the composition comprises from about 0.75 U T4 polynucleotide kinase to about 1.5 U polynucleotide kinase (or any range derivable therein) per 0.001-1 U of Klenow. In some aspects, the composition comprises from about 0.2 U T4 DNA polymerase to about 0.75 U T4 DNA polymerase (or any range derivable therein) per 0.001-1 U of Klenow. In some aspects, the composition comprises from about 0.001 U exonuclease III to about 0.1 U exonuclease III (or any range derivable therein) per 0.001-1 U of Klenow. In some aspects, the composition comprises from about 0.75 U T4 polynucleotide kinase to about 1.5 U T4 polynucleotide kinase (or any range derivable therein), from about 0.2 U T4 DNA polymerase to about 0.75 U T4 DNA polymerase (or any range derivable therein), and from about 0.001 U exonuclease III to about 0.01 U exonuclease III (or any range derivable therein), all per 0.001-1 U of Klenow (or any range derivable therein). In some aspects, the composition comprises about 0.75 U, about 1.2 U, or about 1.5 U T4 polynucleotide kinase; about 0.2 U, about 0.4 U, or about 0.75 U T4 DNA polymerase; and about 0.001 U, 0.005 U, or 0.01 U exonuclease III, all per about 0.001 U, 0.01 U, 0.1 U, or 1 U of Klenow. In one aspect, the composition comprises about 1.2 U T4 polynucleotide kinase, about 0.4 U T4 DNA polymerase, and about 0.005 U exonuclease III per about 1 U of Klenow.

In one embodiment, there are provided methods of generating a ligation-competent nucleic acid molecule comprising obtaining a composition of the embodiments and incubating the composition under conditions to allow for repair of the nucleic acid molecule, thereby producing a ligation-competent nucleic acid molecule.

In one embodiment, there are provided methods of generating a ligation-competent nucleic acid molecule comprising obtaining a nucleic acid molecule; adding at least T4 DNA polymerase, T4 polynucleotide kinase, and exonuclease III to the nucleic acid molecule; and incubating the nucleic acid molecule under conditions (e.g., in a suitable buffer and at a suitable temperature) to allow for repair of the nucleic acid molecule, thereby producing a ligation-competent nucleic acid molecule. The term adding is not meant to impart any directionality on the step. Thus, in some aspects, adding at least T4 DNA polymerase, T4 polynucleotide kinase, and exonuclease III to the nucleic acid molecule means that the nucleic acid molecule is in a container and the T4 DNA polymerase, T4 polynucleotide kinase, and exonuclease III are added to the container. In some aspects, adding at least T4 DNA polymerase, T4 polynucleotide kinase, and exonuclease III to the nucleic acid molecule means that the T4 DNA polymerase, T4 polynucleotide kinase, and exonuclease III are in a container and the nucleic acid molecule is added to the container. In some aspects, both the T4 DNA polymerase, T4 polynucleotide kinase, and exonuclease III and the nucleic acid molecule may be added to a container at the same time.

In some aspects, the method further comprises fragmenting the nucleic acid molecule prior to incubating the nucleic acid molecule under conditions to allow for repair of the nucleic acid molecule. The step of fragmenting the nucleic acid molecule may occur after adding at least T4 DNA polymerase, T4 polynucleotide kinase, and exonuclease III to the nucleic acid molecule. Alternatively, the step of fragmenting the nucleic acid molecule may occur prior to adding at least T4 DNA polymerase, T4 polynucleotide kinase, and exonuclease III to the nucleic acid molecule. In some aspects, fragmenting the nucleic acid molecule comprises exposing the nucleic acid molecule to a hydrodynamic shear force. In some aspects, the fragmented nucleic acid molecules have an average size of about 200 bp, about 300 bp, about 400 bp, about 500 bp, about 1000 bp, or about 2000 bp.

In some aspects, the T4 DNA polymerase, T4 polynucleotide kinase, and exonuclease III are added at a ratio of from about 0.75 U to about 1.5 U T4 polynucleotide kinase (or any range derivable therein), from about 0.2 U to about 0.75 U T4 DNA polymerase (or any range derivable therein), and from about 0.001 U to about 0.1 U exonuclease III (or any range derivable therein). In some aspects, the T4 DNA polymerase, T4 polynucleotide kinase, and exonuclease III are added at a ratio of about 1.2 U T4 polynucleotide kinase, about 0.4 U T4 DNA polymerase, and about 0.005 U exonuclease III.

In some aspects, the method further comprises adding Klenow to the nucleic acid molecule. In some aspects, the T4 DNA polymerase, T4 polynucleotide kinase, exonuclease III, and Klenow are added at a ratio from about 0.75 U to about 1.5 U T4 polynucleotide kinase, from about 0.2 U to about 0.75 U T4 DNA polymerase, from about 0.001 U to about 0.1 U exonuclease III, and from about 0.001 U to about 1 U of Klenow. In some aspects, T4 DNA polymerase, T4 polynucleotide kinase, exonuclease III, and Klenow are added at a ratio about 1.2 U T4 polynucleotide kinase, about 0.4 U T4 DNA polymerase, about 0.005 U exonuclease III, and about 1 U of Klenow.

In some aspects, the ligation-competent nucleic acid molecule comprises a blunt end. In some aspects, the ligation-competent nucleic acid molecule comprises a ligatable internal nick produced by the AP endonuclease activity of exonuclease III.

In some aspects, the method is performed in the presence of an oligonucleotide adaptor. The adaptor may be obtained with the nucleic acid molecule or may be added to the nucleic acid molecule before the T4 DNA polymerase, T4 polynucleotide kinase, and exonuclease III, after that T4 DNA polymerase, T4 polynucleotide kinase, and exonuclease III, or with the T4 DNA polymerase, T4 polynucleotide kinase, and exonuclease III. In some aspects, the oligonucleotide adaptor is a stem-loop adaptor. In some aspects, the oligonucleotide adaptor lacks a phosphate on its 5' end. In some aspects, the adaptor comprises a substantially known sequence. In some aspects, the adaptor comprises a random barcode sequence.

In some aspects, the method further comprises attaching one strand of the oligonucleotide adaptor to the ligation-competent nucleic acid molecule to produce an oligonucleotide-attached nucleic acid molecule. In some aspects, attaching is further defined as ligating. In some aspects, ligating comprises providing T4 DNA ligase to the adaptor and the ligation-competent nucleic acid molecule. In some aspects, attaching produces a nick in the oligonucleotide-attached nucleic acid molecule.

In some aspects, the method is carried out in a single solution comprising one or more of the following: an adaptor, a ligase, polynucleotide kinase, exonuclease III, reverse transcriptase, one or more DNA polymerases, RNA polymerase, ATP, rNTPs, dNTPs, and one or more primers. In some aspects, one or more steps of the method occur in the absence of exogenous manipulation.

In some aspects, the nucleic acid molecule is double-stranded DNA. In some aspects, the double-stranded DNA is human genomic DNA.

In some aspects, the method further comprises preparing a library of ligation-competent nucleic acid molecules. In some aspects, the method further comprises amplifying a plurality of the ligation-competent nucleic acid molecules. In some aspects, the method further comprises determining at least a partial sequence of at least one of the ligation-competent nucleic acid molecules.

In an additional embodiment, there is a kit housed in a suitable container that comprises one or more compositions of the invention and/or comprises one or more compositions suitable for at least one method of the invention.

As used herein, a Unit (U) of T4 DNA polymerase is defined as the amount of enzyme that will incorporate 10 nmol of dNTP into acid-precipitable material in 30 minutes at 37° C. As used herein, a Unit (U) of T4 polynucleotide kinase is defined as the amount of enzyme catalyzing the incorporation of 1 nmol of [$^{32}$P] (ATP donor) in 30 minutes at 37° C. in reaction buffer (70 mM Tris-HCl, 10 mM MgCl$_2$, 5 mM DTT, pH 7.6 @ 25° C.). As used herein, a Unit (U) of exonuclease III is defined as the amount of enzyme required to produce 1 nmol of acid-soluble total nucleotide in 30 minutes at 37° C. As used herein, a Unit (U) of Klenow is defined as the amount of enzyme required to convert 10 nmol of dNTP into acid insoluble material in 30 minutes at 37° C.

As used herein, "essentially free," in terms of a specified component, is used herein to mean the specified component has not been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects. The word "about" means plus or minus 5% of the stated number.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Effects of ExoIII on end-repair reactions. ExoIII was titrated into end-repair reactions of Covaris-sheared DNA containing T4Pol and T4PNK. NGS libraries were prepared and sequenced on an Illumina MiSeq and library diversity was measured by computation of the estimated library size (Picard Tools). From left to right, the bars represent Standard ThruPLEX-DNASeq; 0.001 U ExoIII; 0.01 U ExoIII; 0.1 U ExoIII; and 1 U ExoIII. N=2; *P<0.05 comparing standard end-repair (no ExoIII) to titration points of added ExoIII.

FIG. 2: Effects of ExoIII on run-off amplification. ExoIII was titrated into end-repair reactions of Covaris-sheared DNA containing T4Pol and T4PNK. Initial run-off amplification was performed and threshold cycle determined. Threshold cycles for each reaction condition are provided in Table 1.

U T4Pol/1.5 U T4PNK, and either 0 U, 0.001 U, 0.005 U, or 0.01 U ExoIII. NGS libraries were prepared and sequenced on an Illumina MiSeq and library diversity was measured by computation of the estimated library size (Picard Tools). From left to right, the bars represent the reaction conditions listed in the legend as read from top to bottom. N=2; *P<0.05 comparing end-repair at 0 U of ExoIII to titration points of added ExoIII for each ratio of T4PNK and T4Pol.

DESCRIPTION OF ILLUSTRATIVE EMBODIMENTS

I. Aspects of the Present Invention

Provided herein are compositions comprising and methods relating to the use of *E. coli* Exonuclease III (ExoIII), or homologous enzymes comprising 3' phosphatase and 3' exonuclease activities, in the end-repair of nucleic acid molecules (e.g., double-stranded DNA) damaged by mechanical or enzymatic fragmentation. For example, a composition is provided comprising T4 DNA Polymerase (T4Pol), T4 Polynucleotide Kinase (T4PNK), ExoIII, and the Large Klenow fragment of *E. coli* DNA Polymerase I (Klenow). Use of such a composition in DNA end-repair reactions results in improved and robust end-repair, over a large DNA input range, for the purposes of cloning, amplification, and Next Generation Sequencing (NGS) library preparation.

A "nucleic acid molecule" can be a single nucleic acid molecule or a plurality of nucleic acid molecules. Also, a nucleic acid molecule can be of biological or synthetic origin. Examples of nucleic acid molecules include genomic DNA, cDNA, RNA, a DNA/RNA hybrid, amplified DNA, a pre-existing nucleic acid library, etc. A nucleic acid may be obtained from a human sample, such as blood, serum, plasma, cerebrospinal fluid, cheek scrapings, biopsy, semen, urine, feces, saliva, sweat, etc. A nucleic acid molecule may be subjected to various treatments, such as repair treatments and fragmenting treatments. Fragmenting treatments include mechanical, sonic, and hydrodynamic shearing. Repair treatments include nick repair via extension and/or ligation, polishing to create blunt ends, removal of damaged bases, such as deaminated, derivatized, abasic, or crosslinked nucleotides, etc. A nucleic acid molecule of interest may also be subjected to chemical modification (e.g., bisulfite conversion, methylation/demethylation), extension, amplification (e.g., PCR, isothermal, etc.), etc.

In some aspects, ligase and adaptors may be added to the repair reactions to complete the creation of the adaptor-ligated library molecules to be sequenced without PCR amplification ("PCR-free prep") or to be amplified by PCR to create an amplified library. In some aspects, reagents needed to perform PCR may by added to a reaction comprising end-repair proteins, ligase, and adaptors to complete the creation of an amplified library in the absence of exogenous manipulation. The term "in the absence of exogenous manipulation" as used herein refers to there being modification of a DNA molecule without changing the solution in which the DNA molecule is being modified. In specific embodiments, it occurs in the absence of the hand of man or in the absence of a machine that changes solution conditions, which may also be referred to as buffer conditions. In further specific embodiments, changes in temperature occur during the modification.

In specific embodiments, the invention provides a multi-step procedure that can be performed in a single tube or in a micro-titer plate, for example, in a high-throughput format. One step comprises repair of DNA ends, incorporation of known sequences at both ends of fragments, and at least one enzyme possessing strand-displacement activity. The resulting library of molecules are then amplified by PCR™ using a primer corresponding to the known sequence, resulting in several thousand-fold amplification of the entire genome or transcriptome without significant bias. The products of this amplification can be re-amplified additional times, resulting in amplification that exceeds, for example, several million fold.

Exemplary applications for the invention include but are not limited a closed tube preparation and amplification of genomic libraries (e.g., from highly degraded serum, plasma, and/or urine (such as the supernatant fraction) DNA; formalin fixed, paraffin embedded tissues; fresh biopsy tissues; cell cultures, etc.). DNA amplification and re-amplification can be used as an in vitro "immortalization" process to maintain and generate necessary quantities of valuable but limited DNA samples for gene association studies, mutation and microsatellite instability detection in cancer diagnostics, research application etc. The present invention may also provide for a one-step preparation and simultaneous immobilization of prepared DNA libraries on a solid support.

II. Nucleic Acid End-Repair

Preanalytical processing of nucleic acids for NGS requires fragmentation of the nucleic acid by mechanical or enzymatic shearing followed by ligation of adapters specific to the analytical platform of choice. Some clinical samples, such as human plasma and serum, contain cell-free DNA that is already highly degraded. Whether fragmented artificially or naturally, there is significant damage to the ends of the nucleic acid (e.g., dsDNA), which must be repaired enzymatically to become competent for ligation. Ligation-competent nucleic acid ends are defined as intact blunt-ended double-stranded DNA ends that contain a phosphate at the 5' terminus and a free hydroxyl group at the 3' terminus.

There are two main types of DNA end damage that result in DNA ends that are not competent for ligation:
1. Ends that are not blunt; and
2. Ends that lack a phosphate at a 5'-end and/or have a phosphate at a 3'-end.

The term "blunt end" as used herein refers to the end of a dsDNA molecule having 5' and 3' ends, wherein the 5' and 3' ends terminate at the same nucleotide position. Thus, a blunt end comprises no 5' or 3' overhang.

The first type of damage can be repaired by the concerted action of a DNA polymerase that extends recessed ends in the presence of deoxynucleotide triphosphates (dNTPs) or a 3' exonuclease that trims protruding 3' ends to produce blunt ends. The most commonly used enzyme for this type of repair is T4Pol, which has both DNA polymerase and DNA 3' exonuclease activities residing on the same protein. However, use of T4Pol may result in over-trimming, thus producing one or two base recessed ends that are not competent for ligation. Klenow has the same enzymatic activities as T4Pol but much weaker 3' exonuclease than its counterpart. This property makes it a useful supplement to T4Pol for reducing the risk of over-trimming and making the blunt-end reaction more efficient.

The second type of damage can be repaired by enzymatic activities that transfer phosphates to the 5' termini of DNA and remove phosphates from the 3' termini of DNA, such as 3' phosphatases and/or 3' exonucleases that are not inhibited by the presence of 3' phosphate, such as, for example, PNK. PNK transfers phosphate from deoxynucleotide triphosphates to the 5' termini of DNA in a reversible reaction that depends on the concentration of dNTPs, i.e., high dNTP concentrations shift the equilibrium toward transfer to DNA while high concentrations of diphosphates stimulates the reverse reaction. PNK also has an intrinsic 3'-phosphatase activity that removes phosphate from the 3' termini of DNA but this activity is often insufficient to achieve complete repair.

As provided herein, one example of a multifunctional enzyme that improves the efficiency DNA end-repair is ExoIII. ExoIII catalyzes the stepwise removal of mononucleotides from 3'-hydroxyl termini of double-stranded DNA. ExoIII's 3'-phosphatase activity removes 3'-terminal phosphates, thereby generating 3'-OH groups. It also has class II apurinic/apyrimidinic endonuclease activity, which facilitates hydrolysis of the abasic sites to produce 3'-OH and 5'-$PO_4$ ends.

III. Further Processing of Repaired Nucleic Acids

A. Ligation of Adaptors

Supplementing DNA ends with additional short polynucleotide sequences, referred to as adaptors or linkers, is used in many areas of molecular biology. The usefulness of adapted DNA molecules is illustrated by, but not limited to, several examples, such as ligation-mediated locus-specific PCR, ligation-mediated whole genome amplification, adaptor-mediated DNA cloning, DNA affinity tagging, DNA labeling, etc.

Thus, in another specific embodiment, the attachment of a substantially known sequence to at least one 3' end of at least one DNA fragment comprises ligation of an adaptor molecule to at least one end of the DNA fragment. In a specific embodiment, the adaptor comprises at least one blunt end. In another specific embodiment, the adaptor comprises a single stranded region. In another specific embodiment, the adaptor comprises a stem-loop structure. U.S. Pat. No. 7,803,550 shows the structure of a stem-loop adaptor with a non-replicable linker (which may be introduced chemically during oligonucleotide synthesis or introduced enzymatically during/after the attachment reaction) and shows detailed events occurring at a DNA end during the exemplary multi-enzyme attachment process. In a further specific embodiment, the method further comprises generation of at least one blunt end of said DNA fragments, such as is generated by T4 DNA polymerase, Klenow, or a combination thereof.

The terms "hairpin" and "stem-loop oligonucleotide" as used herein refer to a structure formed by an oligonucleotide comprised of 5' and 3' terminal regions that are inverted repeats and a non-self-complementary central region, wherein the self-complementary inverted repeats form a double-stranded stem and the non-self-complementary central region forms a single-stranded loop.

The adaptor, in a specific embodiment, comprises a substantially known sequence. A skilled artisan recognizes that "substantially known" refers to having sufficient sequence information in order to permit preparation of a DNA molecule, including its amplification. This will typically be about 100%, although in some embodiments some of the primer sequence is random. Thus, in specific embodiments, substantially known refers to about 50% to about 100%, about 60% to about 100%, about 70% to about 100%, about 80% to about 100%, about 90% to about 100%, about 95% to about 100%, about 97% to about 100%, about 98% to about 100%, or about 99% to about 100%.

A blunt-end adaptor can be attached to the ends of double-stranded DNA fragments produced by the fragmentation methods of the present embodiments. Some methods require an additional step that involves a repair of the DNA ends by T4 DNA polymerase and/or Klenow fragment and the removal of 3' or 5' protrusions. The structure of the blunt-end adaptor may be similar to an adaptor of U.S. Pat. Nos. 6,197,557 and 6,828,098, both incorporated by reference herein. One important feature of such an adaptor is the blocking groups at both 3' ends that prevent adaptors from self-ligation. The phosphate group is present at one end of the adaptor to direct its ligation in only one orientation to DNA ends.

A single-stranded DNA adaptor with short 3' overhang containing 4-6 random bases and a phosphorylated recessed 5' end can be attached to the 3' ends of single stranded DNA molecules. The adaptor may have blocking groups at both 3' ends that prevent adaptors from self-ligation. The phosphate group is present at the recessed 5' end of the adaptor. The 4-6 base 3' overhang of the adaptor may have a random base composition. In specific embodiments, it facilitates the annealing and ligation of the adaptor to single stranded DNA molecules. Some methods require an additional step that involves a repair of the 3' ends of single stranded molecules by T4 DNA polymerase, Klenow fragment, and/or exonuclease I. The structure of the single-stranded DNA adaptor may be similar to the adaptor design of U.S. Pat. No. 6,828,098, incorporated by reference herein.

B. Amplification

The term "primer," as used herein, is meant to encompass any nucleic acid that is capable of priming the synthesis of a nascent nucleic acid in a template-dependent process, such as a single-stranded oligonucleotide or a single-stranded polynucleotide that is extended by covalent addition of nucleotide monomers during amplification. Typically, primers are oligonucleotides from ten to twenty and/or thirty base pairs in length, but longer sequences can be employed. Primers may be provided in double-stranded and/or single-stranded form, although the single-stranded form is preferred.

"Oligonucleotide," as used herein, refers collectively and interchangeably to two terms of art, "oligonucleotide" and "polynucleotide." Note that although oligonucleotide and polynucleotide are distinct terms of art, there is no exact dividing line between them and they are used interchangeably herein. The term "adaptor" may also be used interchangeably with the terms "oligonucleotide" and "polynucleotide."

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The method may further comprise the step of designing the primers such that they purposefully are substantially non-self-complementary and substantially noncomplementary to other primers in the plurality. The method may also further comprise the step of amplifying a plurality of the molecules comprising a known nucleic acid sequence to produce amplified molecules. Such amplification may comprise polymerase chain reaction, such as that utilizing a primer complementary to the known nucleic acid sequence.

The primers may comprise a constant region and a variable region, both of which include nucleic acid sequence that is substantially non-self-complementary and substantially non-complementary to other primers in the plurality. The constant region is preferably known and may be a targeted sequence for a primer in amplification methods. The variable region may or may not be known, but in preferred embodiments is known. The variable region may be randomly selected or may be purposefully selected commensurate with the frequency of its representation in a source DNA, such as genomic DNA. In specific embodiments, the nucleotides of the variable region will prime at target sites in a source DNA, such as a genomic DNA, containing the corresponding Watson-Crick base partners. In a particular embodiment, the variable region is considered degenerate.

A number of template-dependent processes are available to amplify the nucleic acids present in a given template sample. One of the best known amplification methods is the polymerase chain reaction (referred to as PCR™) which is described in detail in U.S. Pat. Nos. 4,683,195, 4,683,202, and 4,800,159 and in Innis et al. (1990), each of which is incorporated herein by reference in their entirety. Briefly, two synthetic oligonucleotide primers, which are complementary to two regions of the template DNA (one for each strand) to be amplified, are added to the template DNA (that need not be pure), in the presence of excess deoxynucleotides (dNTP's) and a thermostable polymerase, such as, for example, Taq (Thermus aquaticus) DNA polymerase. In a series (typically 30-35) of temperature cycles, the target DNA is repeatedly denatured (around 90° C.), annealed to the primers (typically at 50-60° C.) and a daughter strand extended from the primers (72° C.). As the daughter strands are created they act as templates in subsequent cycles. Thus, the template region between the two primers is amplified exponentially, rather than linearly.

"Amplification," as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30-100 "cycles" of denaturation and replication.

"Nucleotide," as used herein, is a term of art that refers to a base-sugar-phosphate combination. Nucleotides are the monomeric units of nucleic acid polymers, i.e., of DNA and RNA. The term includes ribonucleotide triphosphates, such as rATP, rCTP, rGTP, or rUTP, and deoxyribonucleotide triphosphates, such as dATP, dCTP, dUTP, dGTP, or dTTP.

A "nucleoside" is a base-sugar combination, i.e., a nucleotide lacking a phosphate. It is recognized in the art that there is a certain inter-changeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e., dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

"Incorporating," as used herein, means becoming part of a nucleic acid polymer.

A reverse transcriptase PCR™ (RT-PCR™) amplification procedure may be performed to quantify an mRNA by amplification of its cDNA. Methods of reverse transcribing RNA into cDNA are well known and described in Sambrook et al., 1989. Alternative methods for reverse transcription utilize thermostable DNA polymerases. These methods are described in PCT Publn. No. WO 1991/009944. Polymerase chain reaction methodologies are well known in the art. Representative methods of RT-PCR™ are described in U.S. Pat. No. 5,882,864.

Nucleic acids useful as templates for amplification are generated by methods described herein. In a specific embodiment, the DNA molecule from which the methods generate the nucleic acids for amplification may be isolated from cells, tissues or other samples according to standard methodologies (Sambrook et al., 1989).

The amplification product may be detected or quantified. In certain applications, the detection may be performed by visual means. Alternatively, the detection may involve indirect identification of the product via chemiluminescence, radioactive scintigraphy of an incorporated radiolabel or fluorescent label, or via a system using electrical and/or thermal impulse signals (Affymax technology).

C. Library Preparation

In another object of the present invention, there is a method of preparing a library of DNA molecules, comprising obtaining a plurality of DNA molecules; randomly fragmenting at least one of the DNA molecules to produce DNA fragments; attaching a primer having a substantially known sequence to at least one end of a plurality of the DNA fragments to produce primer-linked fragments; and amplifying a plurality of the primer-linked fragments. In a specific embodiment, the method further comprises concomitantly sequencing the plurality of primer-linked fragments.

IV. Uses of Fragmented DNA

A. Ligation-Mediated Amplification of Unknown Regions Flanking a Known DNA Sequence Libraries generated by DNA fragmentation and addition of an adaptor (e.g., a universal adaptor) to one or both DNA ends may be used to amplify (by PCR) and sequence DNA regions adjacent to a previously established DNA sequence (see, for example, U.S. Pat. No. 6,777,187 and references therein, all of which are incorporated by reference herein in their entirety). The adaptor can be ligated to the 5' end, the 3' end, or both strands of DNA. The adaptor can have a 3' or 5' overhang. It can also have a blunt end, especially in the cases when DNA ends are polished or conditioned after DNA fragmentation. The terms "polished" and "conditioned" as used herein refers to the repair of dsDNA fragment termini that may be enzymatically repaired, wherein the repair constitutes the fill in of recessed 3' ends or the exonuclease activity trimming back of 5' ends to form a "blunt end" compatible with adaptor ligation. Ligation-mediated PCR amplification is achieved by using a locus-specific primer (or several nested primers) and a primer complementary to the adaptor sequence.

B. Ligation-Mediated Whole Genome Amplification

Libraries generated by DNA fragmentation and subsequent attachment of an adaptor (e.g., a universal adaptor) to both DNA ends were used to amplify whole genomic DNA (whole genome amplification, or WGA) (see, for example, U.S. Patent Appln. Publn. No. 2004/0209299 and U.S. Pat. No. 7,718,403 and references therein, all of which are incorporated by reference herein in their entirety). The adaptor can be ligated to both strands of DNA or only to the 3' end followed by extension. The adaptor can have a 3' or 5' overhang, depending on the structure of the DNA end generated by fragmentation and repair. It can also have a blunt end, such as in the cases where DNA ends are repaired and polished or conditioned after fragmentation. Whole genome PCR amplification is achieved by using one or two universal primers complementary to the adaptor sequence(s), in specific embodiments.

C. Adaptor-Mediated DNA Cloning

Adaptors (or linkers) are frequently used for DNA cloning (see, for example, Sambrook et al., 1989). Ligation of double stranded adaptors to DNA fragments produced by fragmentation, followed by restriction digestion within the adaptors allows production of DNA fragments with 3' or 5' protruding ends that can be efficiently introduced into a vector sequence and cloned.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Titration of ExoIII at Fixed Concentrations of T4Pol and T4PNK

Figure 1:
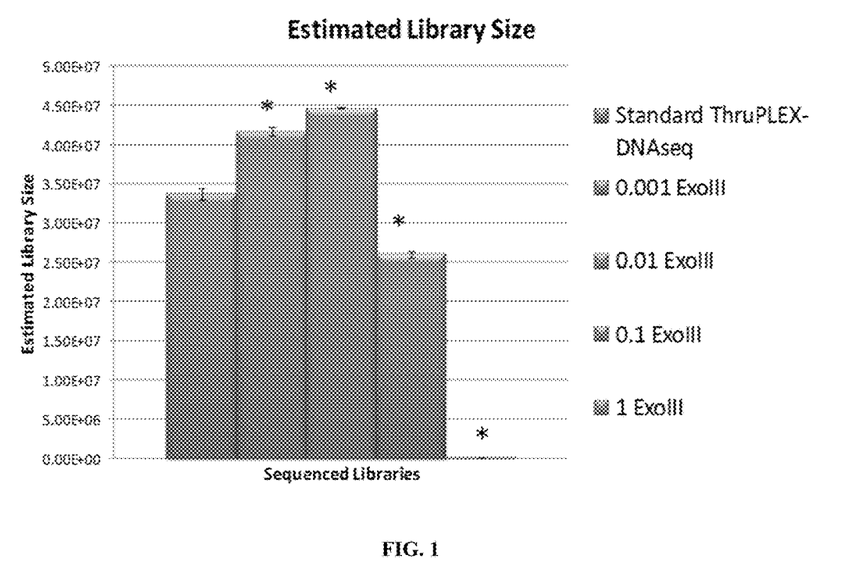

First, the presence of residual 3' phosphate in sonicated DNA was determined and the ability of ExoIII to repair the damaged end and generate a 3'-OH was measured by monitoring amplification curves and high impact sequencing metrics. To this end, 200 pg of 500 bp Covaris-sheared reference NGS libraries were generated in duplicate using a ThruPLEX DNA-Seq library preparation kit (Rubicon Genomics, Inc.). ExoIII was added to the end-repair reactions at 0, 0.001, 0.01, 0.1, and 1.0 U/reaction. T4Pol and T4PNK were present in the reaction at 0.04 U and 2.0 U, respectively. The addition of ExoIII resulted in a biphasic dose-dependent effect on library size diversity (estimated library size; FIG. 1). Library diversity improved by 25% at 0.001 U and 34% at 0.01 U of ExoIII, but dropped by 23% and 99% at 0.1 U and 1 U of ExoIII, respectively. Thus, a significant fraction of the 3' ends of sonicated DNA remain damaged and can be further repaired by small amounts of exonuclease.

Next, ExoIII was titrated with duplicate samples using initial run-off amplification metrics, which was terminated at approximately mid-exponential amplification. End-repair reactions were performed on 50 ng and 50 pg of sheared input DNA using 0.04 U T4Pol, 2.0 U T4PNK, and either 0 U, 0.0001 U, 0.001 U, 0.005 U, 0.01 U, 0.03 U, 0.06 U, or 0.1 U ExoIII. The average threshold cycle was determined for each pair of duplicate samples (FIG. 2 and Table 1).

TABLE 1

Figure 2:
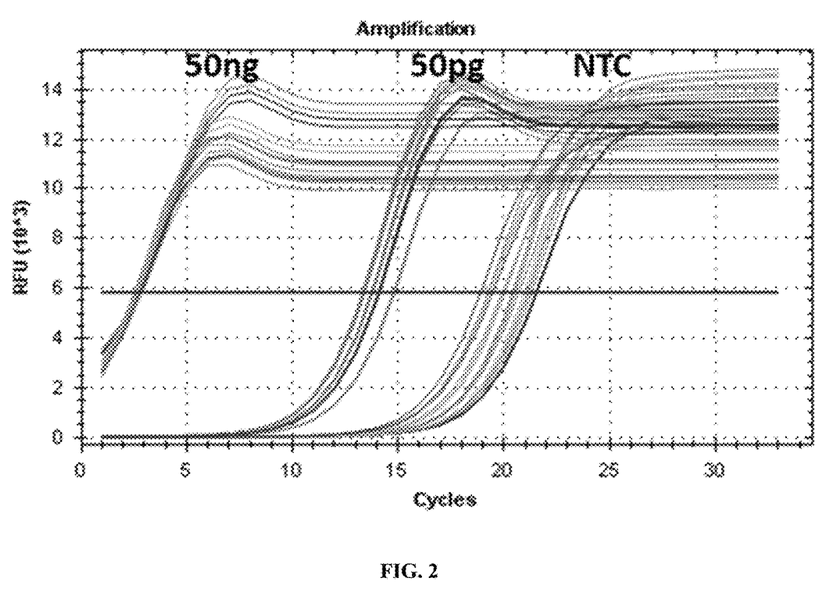

Average Threshold Cycle (corresponds to FIG. 2)

| | | Input DNA | |
|---|---|---|---|
| ExoIII U | NTC | 50 pg | 50 ng |
| 0.0000 | 21.5 | 14.1 | 2.8 |
| 0.0001 | 21.2 | 13.7 | 2.7 |
| 0.001 | 21.1 | 13.4 | 2.6 |
| 0.005 | 20.5 | 13.3 | 2.6 |
| 0.01 | 20.4 | 13.4 | 2.7 |
| 0.03 | 19.7 | 13.8 | 2.6 |
| 0.06 | 19.2 | 14.1 | 2.8 |
| 0.1 | 19.6 | 14.8 | 2.8 |

Example 2

Titration of ExoIII at Varying Ratios of T4PNK and T4Pol

Figure 3:
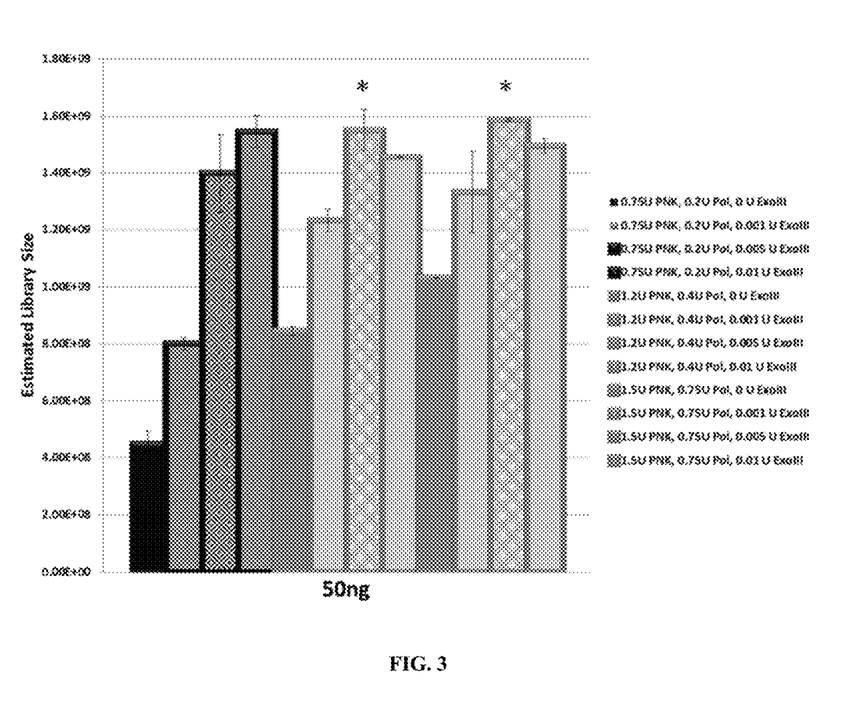
FIG. 3: Titration of ExoIII at three different ratios of T4PNK and T4Pol. End-repair reactions were performed on 50 ng of Covaris-sheared input DNA using either 0.2 U T4Pol/0.75 U T4PNK, 0.4 U T4Pol/1.2 U T4PNK, or 0.75
Figure 4:
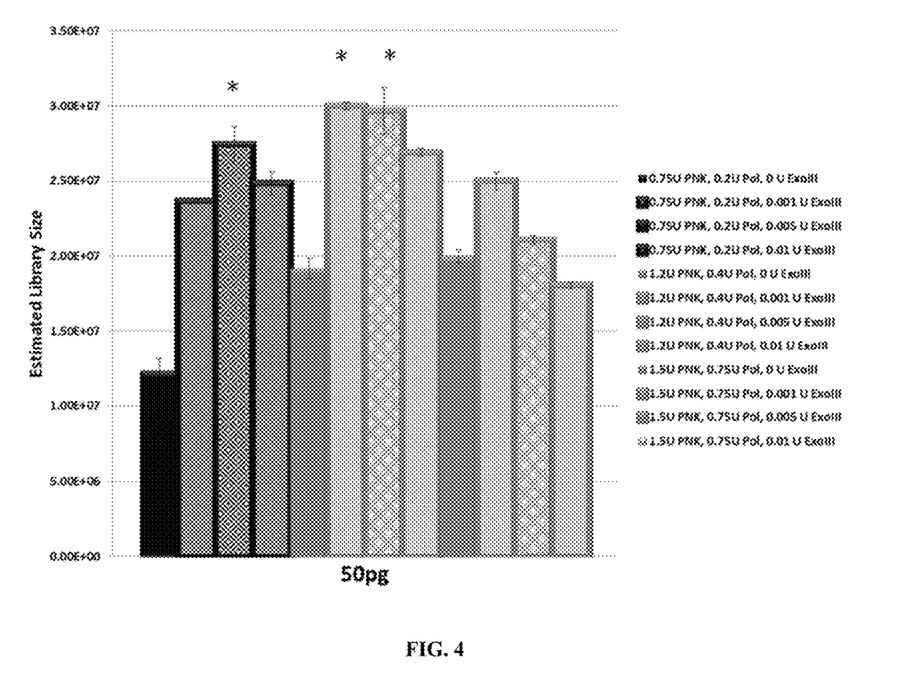
FIG. 4: Titration of ExoIII at three different ratios of T4PNK and T4Pol. End-repair reactions were performed on 50 pg of Covaris-sheared input DNA using either 0.2 U T4Pol/0.75 U T4PNK, 0.4 U T4Pol/1.2 U T4PNK, or 0.75 U T4Pol/1.5 U T4PNK, and either 0 U, 0.001 U, 0.005 U, or 0.01 U ExoIII. NGS libraries were prepared and sequenced on an Illumina MiSeq and library diversity was measured by computation of the estimated library size (Picard Tools). From left to right, the bars represent the reaction conditions listed in the legend as read from top to bottom. N=2; *P<0.05 comparing end-repair at 0 U of ExoIII to titration points of added ExoIII for each fixed ratio of T4PNK and T4Pol.
Figure 5:
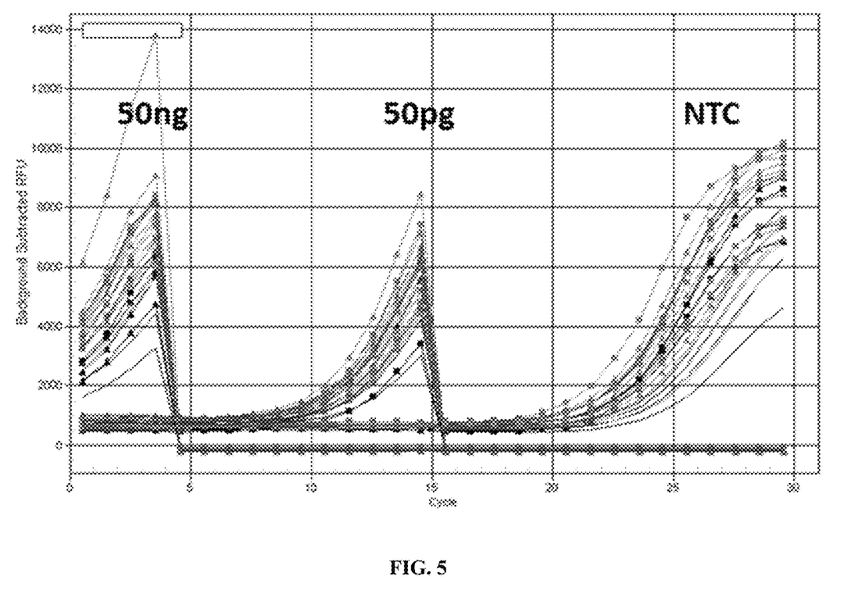
FIG. 5: Titration of ExoIII at three different ratios of T4PNK and T4Pol with high and low inputs of Covaris-sheared DNA. End-repair reactions were performed on 50 ng and 50 pg of sheared input DNA using either 0.2 U T4Pol/0.75 U T4PNK, 0.4 U T4Pol/1.2 U T4PNK, or 0.75 U T4Pol/1.5 U T4PNK, and either 0 U, 0.001 U, 0.005 U, or 0.01 U ExoIII. Initial run-off amplification was performed and threshold cycle determined. Threshold cycles for each reaction condition are provided in Tables 2 and 3.

ExoIII was titrated at three different T4PNK/T4Pol ratios. The matrix was based on previous results of T4PNK/T4Pol titrations and the results of ExoIII titration (see Example 1). Titration of T4PNK and T4Pol was performed in duplicate using initial run-off amplification metrics followed by preparation of samples for sequencing, which were terminated at approximately mid-exponential amplification. End-repair reactions were performed on 50 ng and 50 pg of sheared input DNA using either 0.2 U T4Pol/0.75 U T4PNK, 0.4 U T4Pol/1.2 U T4PNK, or 0.75 U T4Pol/1.5 U T4PNK, and either 0 U, 0.001 U, 0.005 U, or 0.01 U ExoIII. The estimated library sizes for 50 ng and 50 pg of input DNA are shown in FIGS. 3 and 4, respectively. The average threshold cycle determined for each pair of duplicate samples is shown in FIG. 5 and provided in Tables 2-3.

TABLE 2

Average Threshold Cycle for 50 pg of Input DNA (corresponds to FIG. 3)

| ExoIII U | T4PNK/T4Pol U | | |
|---|---|---|---|
| | 0.75/0.2 | 1.2/0.4 | 1.5/0.75 |
| 0.000 | 11.5 | 10.4 | 10.8 |
| 0.001 | 10.1 | 9.6 | 10.0 |
| 0.005 | 9.9 | 9.7 | 10.3 |
| 0.010 | 10.0 | 9.9 | 10.6 |

TABLE 3

Average Threshold Cycle for NTC of Input DNA (corresponds to FIG. 3)

| ExoIII U | T4PNK/T4Pol U | | |
|---|---|---|---|
| | 0.75/0.2 | 1.2/0.4 | 1.5/0.75 |
| 0.000 | 23.9 | 21.9 | 21.7 |
| 0.001 | 22.9 | 21.1 | 21.5 |
| 0.005 | 22.9 | 20.9 | 20.5 |
| 0.010 | 23.3 | 21.6 | 21.5 |

Using both amplification and sequencing metrics, the cross-section of repair enzymes selected for use with the range of Covaris-sheared DNA inputs studied was: 1.2 U of T4PNK, 0.4 U of T4Pol, and 0.005 U of ExoIII per 15 µL reaction.

Example 3

Titration of Klenow

Titration of Klenow was with duplicate samples using initial run-off amplification metrics, followed by NGS samples prepared for sequencing (ThruPLEX DNA-Seq library preparation kit, Rubicon Genomics, Inc.) using 1.2 U of T4PNK, 0.4 U of T4Pol, and 0.005 U of ExoIII per 15 µl reaction. The following units of Klenow per 15 µl reaction were tested: 0 U, 0.001 U, 0.1 U, 1.0 U. Libraries prepared for sequencing were terminated at approximately mid-exponential amplification. The estimated library sizes for 50 ng and 50 pg of input DNA are shown in FIGS. 6A and 6B, respectively.

TABLE 4

Figure 6A:
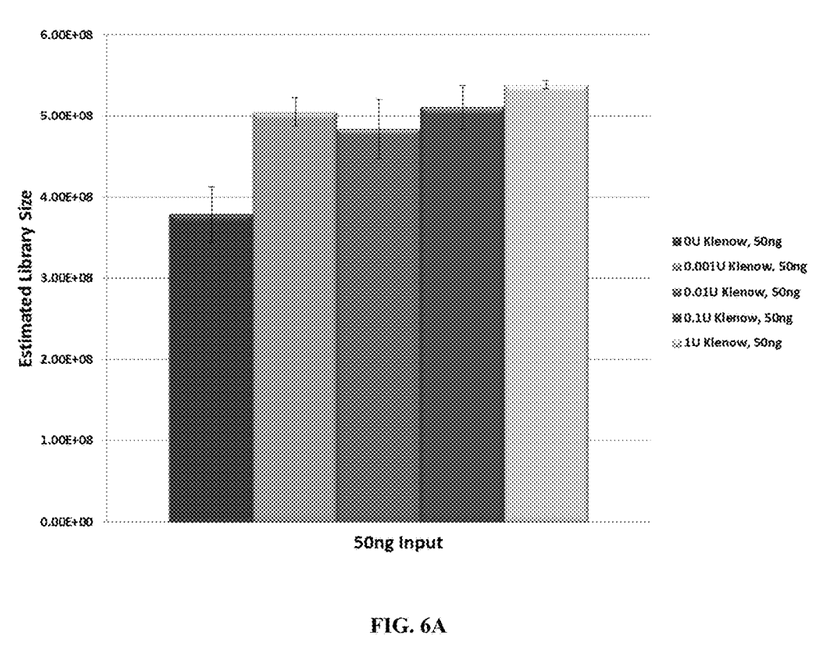
FIGS. 6A-B: Titration of Klenow at 1.2 U of T4PNK, 0.4 U of T4Pol, and 0.005 U of ExoIII per 15 µl reaction with high and low inputs of Covaris-sheared DNA. End-repair reactions were performed on 50 ng (FIG. 6A) and 50 pg (FIG. 6B) of sheared input DNA. The following units of Klenow per 15 µl reaction were tested: 0 U, 0.001 U, 0.1 U, 1.0 U. NGS libraries were prepared and sequenced on an Illumina MiSeq and library diversity was measured by computation of the estimated library size (Picard Tools). From left to right, the bars represent the reaction conditions listed in the legend as read from top to bottom. Threshold cycles for each reaction condition are provided in Table 4.
Figure 6B:
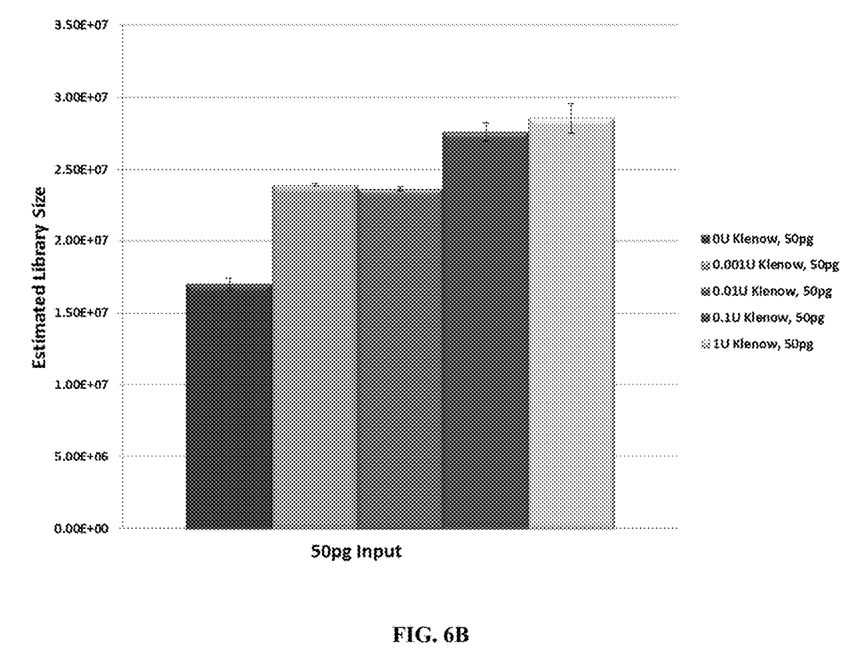

Average Threshold Cycle for 50 ng of Input DNA (corresponds to FIGS. 6A-B)

| Klenow U | Input | | |
|---|---|---|---|
| | 50 ng | 50 pg | NTC |
| 0.000 | 2.03 | 12.86 | 21.03 |
| 0.001 | 2.20 | 12.26 | 21.05 |
| 0.01 | 2.21 | 12.16 | 20.99 |
| 0.10 | 2.41 | 12.31 | 20.89 |
| 1.0 | 2.22 | 12.25 | 21.08 |

Example 4

Four-Enzyme End-Repair Mix

Using both amplification and sequencing metrics from the experiments performed in Examples 1-3, the cross-section of repair enzymes that satisfy the range of Covaris-sheared DNA inputs studied was established at: 1.2 U of T4PNK, 0.4 U of T4Pol, 0.005 U of ExoIII, and 1 U of Klenow per 15 µl reaction.

The four-enzyme end-repair mix resulted in 2.5 to 5-fold improved diversity in library size depending on the DNA input amount (Examples 1-3).

Figure 7:
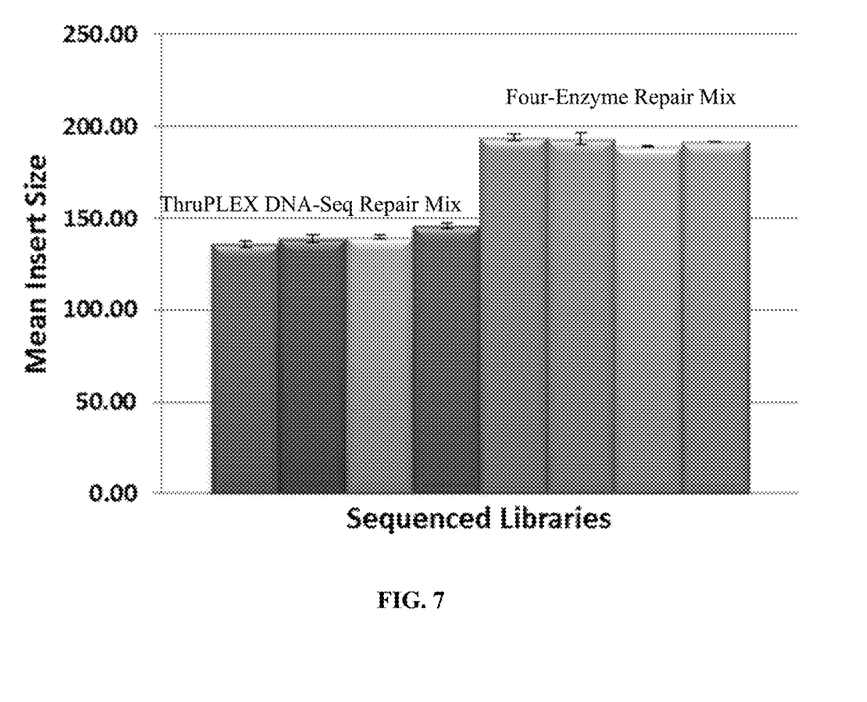
FIG. 7: Comparison of mean insert sizes of NGS libraries prepared from 50 pg inputs of Covaris-sheared DNA in quadruplicate using the DNA end-repair composition of ThruPLEX DNA-Seq library preparation kit and a four-enzyme repair composition described in Example 4 as calculated from paired-end sequencing reads on the MiSeq Illumina platform. The results show that the ThruPLEX DNA-seq kit (with only T4PNK and T4Pol) does not repair the longer fragments as well as the mixture with all four repair enzymes.

The four-enzyme end-repair mix resulted in improved mean insert size by an average of 25% (FIG. 7) by increasing the efficiency of repair of the high molecular weight DNA. The improvement in the library diversity and the increase in library insert size contributed to improved genome coverage at a fixed number of total reads as well as made sequence assembly more accurate.

Figure 8:
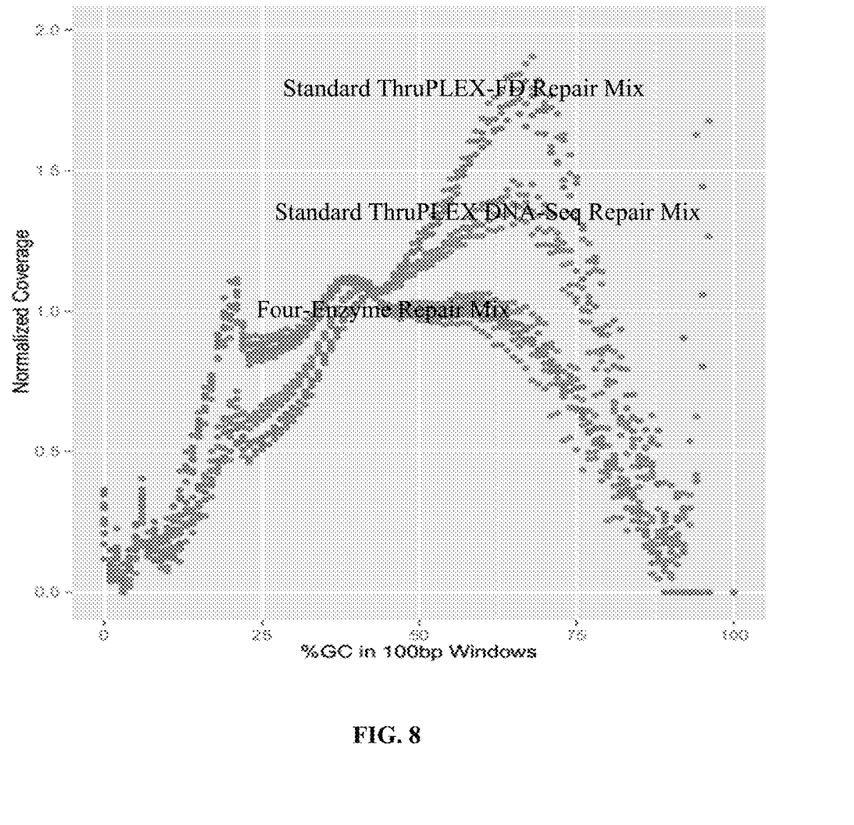
FIG. 8: Normalized % GC distribution of NGS libraries prepared by DNA end-repair ThruPLEX DNA-Seq library preparation kit and a four-enzyme end-repair composition described in Example 4.
Figure 9:
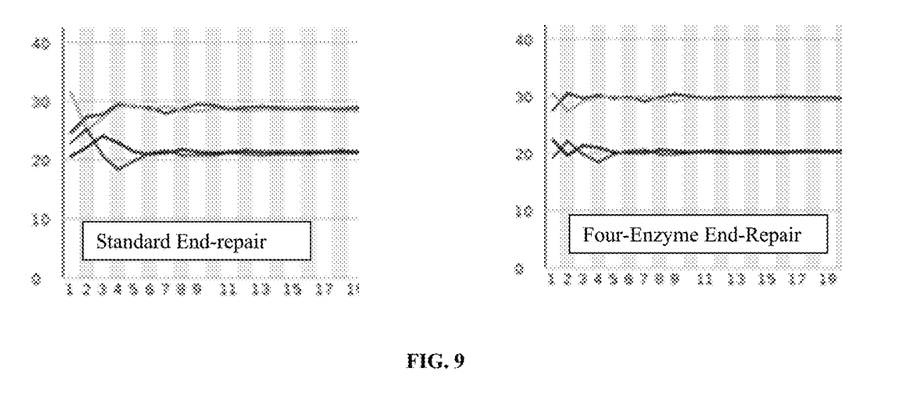
FIG. 9: Initial base bias reduction using four-enzyme end-repair. NGS libraries were prepared by DNA end-repair with a ThruPLEX DNA-Seq library preparation kit and a four-enzyme end-repair composition as described in Example 4. The initial base bias (bias of nucleotides adjacent to the ligated sequencing adaptors) was computed and plotted using the FastQC quality control tool for sequencing (Babraham Bioinformatics, UK). The initial base bias was measurably reduced using the four-enzyme end-repair composition over at least five sequencing runs and with at least two experimental replicates within each run.

The four-enzyme end-repair mix resulted in more balanced GC distribution curves (FIG. 8) and reduced bias of nucleotides adjacent to ligated sequencing adaptors (FIG. 9).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of generating a ligation-competent nucleic acid molecule, the method comprising:
   obtaining a composition comprising T4 DNA polymerase, T4 polynucleotide kinase, exonuclease III, and Klenow; and
   incubating the composition with a nucleic acid in need of end repair under conditions to allow for the end repair of the nucleic acid molecule such that enzymatic activities of the T4 DNA polymerase, T4 polynucleotide kinase, exonuclease III, and Klenow generate a nucleic acid product having blunt ends with a 5'-phosphate group and a 3'-hydroxyl group, thereby producing a ligation-competent nucleic acid molecule.

2. A method of generating a ligation-competent nucleic acid molecule, the method comprising:
   obtaining a nucleic acid molecule in need of end repair;
   adding at least T4 DNA polymerase, T4 polynucleotide kinase, and exonuclease III to the nucleic acid molecule; and
   incubating the nucleic acid molecule with the at least T4 DNA polymerase, T4 polynucleotide kinase, and exonuclease III under conditions to allow for the end repair of the nucleic acid molecule such that enzymatic activities of the T4 DNA polymerase, T4 polynucleotide kinase, and exonuclease III generate a nucleic acid product having blunt ends with a 5'-phosphate group and a 3'-hydroxyl group,
   thereby producing a ligation-competent nucleic acid molecule.

3. The method of claim 2, further comprising fragmenting the nucleic acid molecule prior to incubating the nucleic acid molecule under conditions to allow for repair of the nucleic acid molecule.

4. The method of claim 3, wherein fragmenting the nucleic acid molecule occurs after adding at least T4 DNA polymerase, T4 polynucleotide kinase, and exonuclease III to the nucleic acid molecule.

5. The method of claim 3, wherein fragmenting the nucleic acid molecule occurs prior to adding at least T4 DNA polymerase, T4 polynucleotide kinase, and exonuclease III to the nucleic acid molecule.

6. The method of claim 3, wherein fragmenting the nucleic acid molecule comprises exposing the nucleic acid molecule to a hydrodynamic shear force.

7. The method of claim 3, wherein the fragmented nucleic acid molecules have an average size of about 200 bp, about 300 bp, about 400 bp, about 500 bp, about 1000 bp, or about 2000 bp.

8. The method of claim 2, wherein the T4 DNA polymerase, T4 polynucleotide kinase, and exonuclease III are added at a ratio of from about 0.75 U to about 1.5 U T4 polynucleotide kinase, from about 0.2 U to about 0.75 U T4 DNA polymerase, and from about 0.001 U to about 0.1 U exonuclease III.

9. The method of claim 8, wherein the T4 DNA polymerase, T4 polynucleotide kinase, and exonuclease III are added at a ratio of about 1.2 U T4 polynucleotide kinase, about 0.4 U T4 DNA polymerase, and about 0.005 U exonuclease III.

10. The method of claim 2, further comprising adding Klenow to the nucleic acid molecule.

11. The method of claim 10, wherein the T4 DNA polymerase, T4 polynucleotide kinase, exonuclease III, and Klenow are added at a ratio from about 0.75 U to about 1.5 U T4 polynucleotide kinase, from about 0.2 U to about 0.75 U T4 DNA polymerase, from about 0.001 U to about 0.1 U exonuclease III, and from about 0.001 U to about 1 U of Klenow.

12. The method of claim 11, wherein the T4 DNA polymerase, T4 polynucleotide kinase, exonuclease Ill, and Klenow are added at a ratio about 1.2 U T4 polynucleotide kinase, about 0.4 U T4 DNA polymerase, about 0.005 U exonuclease III, and about 1 U of Klenow.

13. The method of claim 2, wherein the ligation-competent nucleic acid molecule comprises a blunt end.

14. The method of claim 2, wherein the method is performed in the presence of an oligonucleotide adaptor.

15. The method of claim 14, wherein the oligonucleotide adaptor is a stem-loop adaptor.

16. The method of claim 14, wherein the oligonucleotide adaptor lacks a phosphate on its 5' end.

17. The method of claim 14, wherein the adaptor comprises a substantially known sequence.

18. The method of claim 14, wherein the adaptor comprises a random barcode sequence.

19. The method of claim 14, further comprising attaching one strand of the oligonucleotide adaptor to the ligation-competent nucleic acid molecule to produce an oligonucleotide-attached nucleic acid molecule.

20. The method of claim 19, wherein attaching is performed by ligating at least one strand of the oliqonucleotide adaptor to the ligation-competent nucleic acid molecule.

21. The method of claim 20, wherein ligating comprises providing T4 DNA ligase to the adaptor and the ligation-competent nucleic acid molecule.

22. The method of claim 19, wherein attaching produces a nick in the oligonucleotide-attached nucleic acid molecule.

23. The method of claim 19, wherein the method is carried out in a single solution.

24. The method of claim 23, wherein the solution comprises one or more of the following: an adaptor, a ligase, polynucleotide kinase, exonuclease III, reverse transcriptase, one or more DNA polymerases, RNA polymerase, ATP, rNTPs, dNTPs, and one or more primers.

25. The method of claim 19, wherein one or more steps of the method occur in the absence of exogenous manipulation.

26. The method of claim 2, wherein the nucleic acid molecule is double-stranded DNA.

27. The method of claim 26, wherein the ligation-competent nucleic acid molecule comprises a ligatable internal nick produced by the AP endonuclease activity of exonuclease III.

28. The method of claim 26, wherein the double-stranded DNA is human genomic DNA.

29. The method of claim 2, further comprising preparing a library of ligation-competent nucleic acid molecules.

30. The method of claim 2, further comprising amplifying a plurality of the ligation-competent nucleic acid molecules.

31. The method of claim 2, further comprising determining at least a partial sequence of at least one of the ligation-competent nucleic acid molecules.

32. A method of preparing a library of ligation-competent DNA fragments, the method comprising:
   a) providing a composition comprising a plurality of DNA fragments in need of end repair to be ligated;
   b) adding T4 DNA polymerase, T4 polynucleotide kinase, and exonuclease III to the composition; and
   c) incubating the composition under conditions to allow for the end repair of the plurality of DNA fragments such that enzymatic activities of the T4 DNA polymerase, T4 polynucleotide kinase, and exonuclease III generate a plurality of ligation-competent DNA fragments, wherein each DNA fragment has blunt ends with a 5'-phosphate group and a 3'-hydroxyl group, thereby producing a library of ligation-competent DNA fragments.

33. The method of claim 32, further comprising adding Klenow to the composition.

34. The method of claim 32, further comprising ligating at least one adapter to each of the ligation-competent DNA fragments.

35. The method of claim 34, further comprising using said at least one adapter for adapter-mediated cloning, amplification, or sequencing.

36. The method of claim 34, wherein said at least one adapter is a universal adapter for amplification or sequencing.

* * * * *